(12) United States Patent
Aytug et al.

(10) Patent No.: US 12,090,461 B2
(45) Date of Patent: *Sep. 17, 2024

(54) FLUID STORAGE MEDIA AND METHOD OF DELIVERING A FLUID

(71) Applicant: UT-BATTELLE, LLC, Oak Ridge, TN (US)

(72) Inventors: Tolga Aytug, Knoxville, TN (US); Kai Li, Farragut, TN (US); Meghan E. Lamm, Oak Ridge, TN (US); Diana Hun, Lenoir City, TN (US); Kaushik Biswas, Davis, CA (US)

(73) Assignee: UT-BATTELLE, LLC, Oak Ridge, TN (US)

(*) Notice: Subject to any disclaimer, the term of this patent is extended or adjusted under 35 U.S.C. 154(b) by 418 days.

This patent is subject to a terminal disclaimer.

(21) Appl. No.: 17/509,869

(22) Filed: Oct. 25, 2021

(65) Prior Publication Data

US 2022/0097016 A1    Mar. 31, 2022

Related U.S. Application Data

(63) Continuation of application No. 17/384,317, filed on Jul. 23, 2021.

(Continued)

(51) Int. Cl.
*B01J 13/20* (2006.01)
*A61K 9/00* (2006.01)
(Continued)

(52) U.S. Cl.
CPC ........... *B01J 13/203* (2013.01); *A61K 9/0004* (2013.01); *A61K 9/5073* (2013.01); *B01J 13/22* (2013.01); *B32B 27/10* (2013.01); *B32B 27/20* (2013.01); *C04B 20/0032* (2013.01); *C04B 20/1029* (2013.01); *D21H 17/74* (2013.01);
(Continued)

(58) Field of Classification Search
None
See application file for complete search history.

(56) References Cited

U.S. PATENT DOCUMENTS

| 3,607,169 A | 9/1971 | Coxe |
| 5,500,287 A | 3/1996 | Henderson |
| 5,713,974 A * | 2/1998 | Martin .................. F16L 59/065 65/17.2 |

OTHER PUBLICATIONS www.sono-tek.com/wp-content/uploads/2012/01/Ultrasonic-spray-coating-of-nanoparticles.pdf.
(Continued)

*Primary Examiner* — Alexander M Weddle
(74) *Attorney, Agent, or Firm* — FOX ROTHSCHILD LLP

(57) ABSTRACT

A fluid storage media includes a plurality of microspheres. Each microsphere includes a porous core with a porous core material and having an exterior surface. A stored fluid is within the porous core. A coating layer covers all of the exterior surface of the porous core. The coating layer includes a coating material which transitions from a first state to a second state, wherein in the first state the coating material is permeable to the stored fluid, and in the second state the material is impermeable to the stored fluid. The coating material in the second state is configured to encapsulate and maintain the stored fluid inside the porous core. A method of making a fluid storage media, a method of delivering a fluid and a method of delivering a biologically active fluid medication to a patient are also disclosed.

37 Claims, 13 Drawing Sheets

Related U.S. Application Data

(60) Provisional application No. 63/056,252, filed on Jul. 24, 2020.

(51) Int. Cl.

| | | |
|---|---|---|
| *A61K 9/50* | (2006.01) | |
| *B01J 13/22* | (2006.01) | |
| *B32B 27/10* | (2006.01) | |
| *B32B 27/20* | (2006.01) | |
| *C04B 20/00* | (2006.01) | |
| *C04B 20/10* | (2006.01) | |
| *D21H 17/00* | (2006.01) | |
| *E04B 1/80* | (2006.01) | |
| *E04C 2/288* | (2006.01) | |
| *C04B 111/00* | (2006.01) | |

(52) U.S. Cl.
CPC .............. *E04B 1/806* (2013.01); *E04C 2/288* (2013.01); *B32B 2264/2032* (2020.08); *B32B 2264/303* (2020.08); *B32B 2307/304* (2013.01); *B32B 2419/00* (2013.01); *B32B 2553/00* (2013.01); *C04B 2111/00612* (2013.01); *C04B 2201/30* (2013.01)

(56) References Cited

OTHER PUBLICATIONS

Aytug et al. 2015, J. Mater. Chem. C, 3, 5440.
Chang et al., 2016. "Low cost composites for vacuum insulation core material." Vacuum 131:120-126.
http://www.mo-sci.com/porous-silica.
Hun, D. et al.:"Evacuated Spheres for Closed-Cell Vacuum Insulation", 2019 Buildings XIV International Conference, Clearwater Beach, FL, Dec. 9-12, 2019.
Ruckdeschel, P. et al.: "Understanding thermal insulation in porous, particulate materials", Adv. Funct. Mater. 2017, 27 (38), 1702256.
Lu, D. et al.: "ZnO nanostructures decorated hollow glass microspheres as near infrared reflective pigment", Ceram. Int. 2017, 43 (12), 9164-9170.
Zhang, C. et al.: "Effects of hollow microspheres on the thermal insulation of polysiloxane foam", J. Appl. Polym. Sci. 2017, 134 (18).
Gao, T. et al: "Monodisperse hollow silica nanospheres for nano insulation materials: synthesis, characterization, and life cycle assessment", ACS Appl Mater Interfaces 2013, 5 (3), 761-7.
Wicks, G. et al.: "Glass microspheres hollow out a niche for anticounterfeiting strategies", Am. Ceram. Soc. Bull. 2016, 95 (6), 24-29.
Li et al.: "Effect of microstructure and physical parameters of hollow glass microsphere on insulation performance", Materials Letters 65 (2011) 1992-1994.
Ozkutlu et al.: "Effects of hollow glass microsphere density and surface modification on the mechanical and thermal properties of poly(methyl methacrylate) syntactic foams", Composite Structures 202 (2018) 545-550.
Sun et al.: "Enhanced Thermal Insulation of the Hollow Glass Microsphere/Glass Fiber Fabric Textile Composite Material", Polymers 2021, 13.
Gao et al.: "Preparation and properties of hollow glass bead filled silicone rubber foams with low thermal conductivity", Materials and Design 46 (2013) 491-496.
Hu et al.: "Silicon rubber/hollow glass microsphere composites: Influence of broken hollow glass microsphere on mechanical and thermal insulation property", Composites Science and Technology 79 (2013) 64-69.
Hu et al.: "Hollow-Structured Materials for Thermal Insulation", Adv. Mater. 2019, 31, 1801001.
Li et al.: "Hermetically sealed porous-wall hollow microspheres enabled by monolithic glass coatings: Potential for thermal insulation applications", Vacuum 195 (2022) 110667.
Li et al.: "Porous-wall hollow glass microspheres as novel potential nanocarriers for biomedical applications", Nanomedicine: Nanotechnology, Biology, and Medicine 6 (2010) 127-136.

\* cited by examiner

FLUID STORAGE MEDIA AND METHOD OF DELIVERING A FLUID

CROSS-REFERENCE TO RELATED APPLICATIONS

This application is a continuation of U.S. patent application Ser. No. 17/384,317 filed on Jul. 23, 2021, which claims priority to U.S. 63/056,252 filed on Jul. 24, 2020, entitled "Coated and Evacuated Insulation Spheres (CEIS)", the entire disclosures of which are incorporated herein by reference.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in this invention.

FIELD OF THE INVENTION

The present invention relates generally to insulation spheres and methods of making insulation spheres.

BACKGROUND OF THE INVENTION

Enhancing the thermal performance of existing buildings is typically hindered by space and technoeconomic restrictions. To meet building code requirements, these limitations favor insulation materials that can be constructed in slim profiles and that enable thermal conductivities (TCs) lower than those of commonly used insulations in buildings [<0.024 W/m·K (>R6/in.)]. To date, the most common commercially available material that achieves this thermal property in a thinner design is the vacuum-insulated panel (VIPs), wherein heat transfer is suppressed by creating a vacuum (e.g., <5 mbar) in the encapsulated open-cell micro- or nanoporous core components that minimize gaseous conduction. In fact, VIPs can demonstrate exceptionally low thermal performance, down to ~0.002-0.005 W/m·K (~R35/in.), with just a fraction of the required insulation thickness of traditional non-vacuum insulation materials (e.g., fiberglass, mineral wool, polymer foams, TC~0.02-0.04 W/m·K). However, their adoption in buildings as an insulation material has been hindered by the fragility of the vacuum barrier, which is easily damaged by accidental punctures/cuts, and degradation in the thermal properties over time due to the continuous permeation of water vapor and gas molecules through the barrier envelope. Accordingly, VIPs are not flexible for on-site adaptation as they cannot be cut to size without sacrificing a substantial part of their thermal performance. To alleviate these concerns, based on the principal of the Knudsen effect, core materials with pore sizes in the nanometer range (typically less than 50 nm) have been proposed to reduce or even eliminate gaseous thermal conductivity with low-quality or without need of a vacuum. Because of their intrinsic small pore size (5-40 nm), very high porosity (85-99.8%), and associated low bulk density (as low as 3 kg/m$^3$), aerogels were considered the preferred choice as a core material for vacuum insulation systems. However, their high production cost and weak mechanical properties significantly hindered the integration of aerogels as a thermal insulating solution for building applications. Hence, there is a strong need for sustainable, high-performance thermal insulation technologies that can increase building efficiency compared with conventional insulation materials or VIPs.

Vacuum insulation systems based on closed-cell core materials have been created. These use a material with a closed pore structure that maintains a vacuum within it, without the need for a vacuum barrier envelope. Such a material not only can enable high-quality thermal performance (similar to VIPs) but also may prove significantly more suitable for construction because the fabricated insulation boards can be cut to desired sizes. Any damage to a panel will cause only localized vacuum damage (i.e., only a few spheres will lose vacuum) instead of damage to the entire panel, which will minimally impact the effective thermal performance. In this context, hollow silica microspheres with a solid shell have attracted considerable interest for insulation applications. Owing to their inorganic nature and hollow core structure, these materials have low density and high chemical and thermal stability. Some closed-cell core materials have interior cavities that are filled with a low-thermal-conductivity gas, however, a perfect vacuum will theoretically eliminate gas conduction through a medium. It is imperative, therefore, that the hollow cavities of the spheres be effectively evacuated to attain a high level of thermal insulation. However, once fabricated, a material like this cannot be evacuated because of its closed, rigid shell structure. Evacuated hollow particles have proven to be difficult to commercialize because all are either based on expensive, elaborate processing schemes and/or are pertinent only to laboratory-scale fabrication.

SUMMARY OF THE INVENTION

An insulation medium includes a plurality of microspheres. Each microsphere includes a porous core comprising a porous core material and having an exterior surface, a gas within the porous core, and a coating layer coating all of the exterior surface of the porous core. The coating layer can include a coating material which transitions from a first state to a second state. In the first state the coating material is permeable to the gas, and in the second state the material is impermeable to the gas. The coating material in the second state is configured to encapsulate and maintain partial vacuum of the gas inside the porous core. In the second state the coating is impermeable to air.

The partial vacuum can be less than 760 torr. The partial vacuum can be less than 100 torr. The partial vacuum can be from $10^{-6}$ to less than 760 torr.

The porous core can include a structure of interconnected pores or channels. The coating material can conformally coat the exterior of the porous core to form a gas-impermeable layer that maintains the partial vacuum inside the porous core. The porous core can comprises at least one of the group of glass, diatomaceous earth, calcium silicate and polymers. The glass can be at least one of borosilicate, quartz, Pyrex® and soda lime. The porous core can be shaped as a hollow shell comprising a porous shell wall. The thickness of the shell wall can be from 0.5-5 µm.

The coating material can include a polymeric material. The polymeric material can include at least one of methyl methacrylate copolymer, ethyl methacrylate copolymer, polyvinyl butyral, poly(methyl methacrylate-co-ethyl acrylate), polystyrene, polyvinyl butyral, polyvinyl alcohol, poly(ethylene carbonate), ethylene vinyl alcohol copolymer, polyurethane and epoxies.

The coating material can include an inorganic material. The inorganic material can include at least one of soda-lime glass, borosilicate glass, quartz, alumina, Pyrex®, silica, and metal-oxide compounds. The inorganic material can include at least one metal selected from the group of aluminum, chromium, cobalt, copper, gold, iron, manganese, nickel, palladium, platinum, silver, titanium, zinc and zirconium. The inorganic material can be in the form of a powder.

The coating material can have a thickness of from 10-1000 nm. The diameter of the microsphere can be from 30-300 µm. The porous core can include pores having a pore diameter of from 5 nm to 1000 nm. The porosity of the porous core can be from 25% to 90%.

The transition from the first state to the second state can comprise at least one selected from the group of polymerization, densification and sintering. The transition from the first state to the second state can comprise melting and resolidifying a polymer coating.

The gas can include at least one selected from the group of air, $H_2$, $H_2S$, $O_2$, CO, $CO_2$, NO, $NO_2$, $NH_3$, $CH_4$, $CO_2$, and mercaptan.

The matrix material can be configured to randomly pack the plurality of microspheres in the matrix material. The randomly packed microspheres can form a void fraction in a range of 15-99 volume % based upon the total volume of the microspheres and the matrix material. The matrix material can be a polymeric material. The matrix polymeric material can include at least one selected from the group consisting of methyl methacrylate copolymer, ethyl methacrylate copolymer, polyvinyl butyral, poly(methyl methacrylate-co-ethyl acrylate), polystyrene, polyvinyl butyral, polyvinyl alcohol, poly(ethylene carbonate), ethylene vinyl alcohol copolymer, polyurethane and epoxies.

Insulation according to the invention can include an insulation medium which includes a plurality of microspheres. Each microsphere includes a porous core comprising a porous core material and having an exterior surface, a gas within the porous core, and a coating layer covering all of the exterior surface of the porous core. The coating layer comprises a coating material which transitions from a first state to a second state. In the first state the coating material is permeable to the gas, and in the second state the material is impermeable to the gas. The coating material in the second state is configured to encapsulate and maintain partial vacuum of the gas inside the porous cor. A container is provided for the insulation medium.

The insulation has a thermal resistance in a range of 15-400 mK/W. The container can include wall board. The container can include paper. The matrix material can be configured to randomly pack the plurality of microspheres in the matrix material.

A building panel can include a first facing material, a second facing material spaced from the first facing material, and an insulation medium between the first facing panel and the second facing panel. The insulation medium includes a plurality of microspheres. Each microsphere includes a porous core comprising a porous core material and having an exterior surface, a gas within the porous core, and a coating layer coating all of the exterior surface of the porous core. The coating layer can include a coating material which transitions from a first state to a second state. In the first state the coating material is permeable to the gas, and in the second state the material is impermeable to the gas. The coating material in the second state is configured to encapsulate and maintain partial vacuum of the gas inside the porous core.

A method of making an insulation medium can include the step of providing a plurality of microspheres. Each microsphere includes a porous core comprising a porous core material and having an exterior surface. A gas is positioned within the porous core. A coating layer is applied to cover all of the exterior surface of the porous core to provide a coated porous core. The coating layer includes a coating material which transitions from a first state to a second state. In the first state the coating material is permeable to the gas, and in the second state the material is impermeable to the gas. A vacuum is applied to the coated porous core. Some of the gas will diffuse through the coating material in the first state to establish a partial vacuum of the gas within the porous core. The coating material is transitioned from the first state to the second state while maintaining the partial vacuum of the gas within the porous core. The coating in the second state will seal the porous core with the partial vacuum of the gas inside.

The step of applying a coating layer to the porous core can include sputtering the coating material. The step of applying a coating layer to the porous core can include dip-coating the porous core in the coating material. The step of applying a coating layer to the porous core can include fluidized-bed coating of the coating material onto the porous core.

The step of transitioning the coating material from the first state to the second state can include at least one selected from the group consisting of polymerization, densification and sintering. The step of transitioning the coating material from the first state to the second state can include heating of the coating material. The method can further include embedding the microspheres into a matrix material.

A fluid storage media includes a plurality of microspheres. Each microsphere includes a porous core comprising a porous core material and having an exterior surface, a stored fluid within the porous core, and a coating layer coating all of the exterior surface of the porous core. The coating layer includes a coating material which transitions from a first state to a second state. In the first state the coating material is permeable to the stored fluid, and in the second state the material is impermeable to the stored fluid. The coating material in the second state is configured to encapsulate and maintain the stored fluid inside the porous core.

The stored fluid pressure in the porous core can be above an ambient pressure surrounding the microspheres. The coating can be biodegradable. The coating material can degrade at an operating temperature. The coating can be frangible. The coating can dissolve in a solvent.

The stored fluid can include at least one selected from the group consisting of $H_2$, $H_2S$, $O_2$, CO, $CO_2$, NO, $NO_2$, $NH_3$, $CH_4$, $CO_2$, $SO_2$ and mercaptan. The sored fluid comprises a gaseous hydrocarbon selected from the group consisting of acetylene, propane, ethylene, and light alkanes. The stored fluid is a biologically active medication. The stored fluid can include at least one refrigerant selected from the group consisting of fluorocarbons, butane, propane, and ammonia.

A method of delivering a fluid includes the step of providing a plurality of microspheres. Each microsphere includes a porous core comprising a porous core material and having an exterior surface. A coating layer is applied to all of the exterior surface of the porous core to provide a coated porous core. The coating layer includes a coating material which transitions from a first state to a second state. In the first state the coating material is permeable to the fluid, and in the second state the material is impermeable to the fluid. A pressure of the fluid is applied to the coated porous core, wherein some of the fluid will diffuse through the coating material in the first state to establish a quantity of the fluid within the porous core. The coating material is transitioned from the first state to the second state while maintaining the quantity of the fluid within the porous core, and the coating in the second state will seal the porous core with the quantity of the fluid inside. The microspheres are delivered to a location. The coating is degraded to release the fluid. The fluid pressure can be applied before the coating material has been applied to the porous core. The fluid pressure can be applied after the coating material has been applied to the porous core.

A method of delivering a biologically active fluid medication to a patient includes the step of providing a plurality of microspheres. Each microsphere includes a porous core comprising a porous core material and having an exterior surface. The biologically active fluid medication is positioned within the porous core. A coating layer is applied to the exterior surface of the porous core to provide a coated porous core. The coating layer comprises a coating material which transitions from a first state to a second state. In the first state the coating material is permeable to the biologically active fluid medication, and in the second state the material is impermeable to the biologically active fluid medication. A pressure of the biologically active fluid medication is applied to the coated porous core, and some of the biologically active fluid medication will diffuse through the coating material in the first state to establish a quantity of the biologically active fluid medication within the porous core. The coating material is transitioned from the first state to the second state while maintaining the quantity of the biologically active fluid medication within the porous core, such that the coating in the second state will seal the porous core with the quantity of the biologically active fluid medication inside.

The coating material in the second state can include a biodegradable material. After being delivered to the body of the patient, the coating will biodegrade and deliver the biologically active fluid medication to the patient. The coating material in the second state can be temperature sensitive and degrade at body temperature. After being delivered to the body of the patient the coating will degrade at body temperature and deliver the biologically active fluid medication to the patient.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
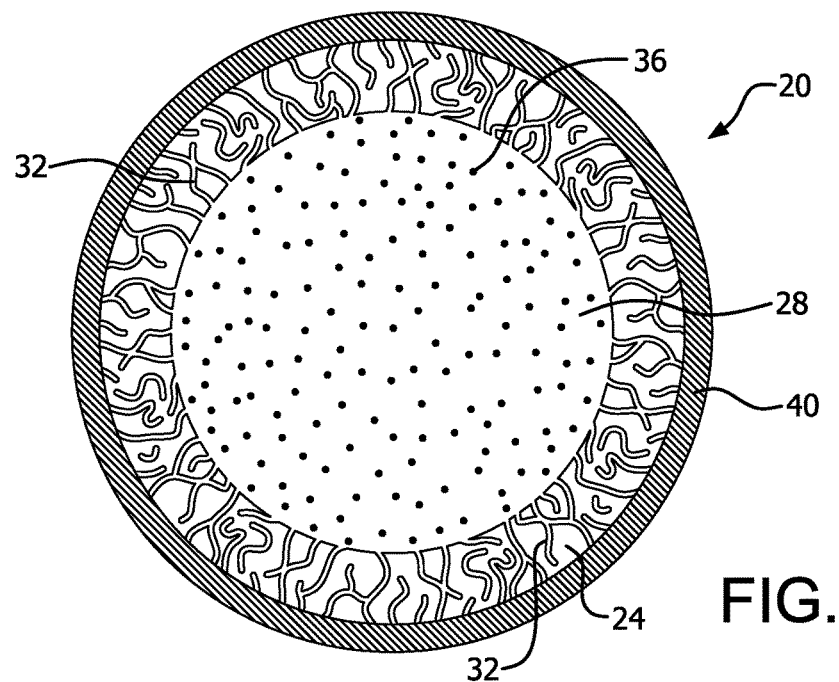
FIG. 1 is a schematic diagram of a microsphere in a first stage of assembly.

The present invention provides microspheres with nanoscale wall porosity, which provides a gas diffusion pathway for either filling or evacuating the pores and any interior cavities. The pores can be interconnected. The fabrication methods can be based on industry-standard equipment and are inherently scalable manufacturing processes that enable highly dense sealed coatings. In addition to thermal insulation applications, because the microspheres can be made from materials that are non-toxic, naturally abundant, and inexpensive, these glass particles can benefit various applications ranging from gas storage, transport, separation/purification/sequestration to drug delivery in the medical field.

An insulation medium according to the invention includes a plurality of microspheres. Each microsphere comprises a porous core comprising a porous core material and having an exterior surface, a gas within the porous core, and a coating layer covering all of the exterior surface of the porous core. The coating layer comprises a coating material which transitions from a first state to a second state. In the first state, the coating material is permeable to the gas. In the second state the material is impermeable to the gas. The coating material in the second state is configured to encapsulate and maintain partial vacuum of the gas inside the porous core. In one embodiment, in the second state the coating is impermeable to air.

The partial vacuum can be less than 760 torr. The partial vacuum can be less than 100 torr. The partial vacuum can be from $10^{-6}$ to 760 torr. The partial vacuum can be $10^{-6}$, $10^{-5}$, $10^{-4}$, $10^{-3}$, $10^{-2}$, 0.1, 1, 10, 50 100, 150, 200, 250, 300, 350, 400, 450, 500, 550, 600, 650, 700, or 760 torr, and can be within a range of any high value and low value selected from these values.

The pore structure can vary. The pores or channels should percolate or extend either directly or in an interconnected or tortuous fashion through the porous core. The porous core can be a spherical or other shape solid porous structure, or can have a hollow interior space with a porous shell structure. The coating material conformally coats the exterior of the porous core to form a gas-impermeable layer that maintains the partial vacuum inside the porous core.

The porous core can be made from a variety of different materials. The porous core can include at least one selected from the group consisting of glass, diatomaceous earth, calcium silicate and polymers. The glass can include at least one selected from the group consisting of borosilicate, quartz, Pyrex® and soda lime.

The porous core can take different shapes and sizes. The porous core can be shaped as a hollow shell comprising a porous shell wall. The thickness of the shell wall can be from 0.5-5 µm. The thickness of the shell wall can be 0.5, 0.75, 1, 1.25, 1.5, 1.75, 2, 2.25, 2.5, 2.75, 3, 3.25, 3.5, 3.75, 4, 4.25, 4.5, 4.75, or 5 µm, or can be within a range of any high value and low value selected from these values. Other dimensions are possible.

The coating material can include a polymeric material. The polymeric material can include at least one selected from the group consisting of polyolefins, methyl methacrylate copolymer, ethyl methacrylate copolymer, polyvinyl butyral, poly(methyl methacrylate-co-ethyl acrylate), polystyrene, polyvinyl butyral, polyvinyl alcohol, poly(ethylene carbonate), ethylene vinyl alcohol copolymer, polyurethane and epoxies.

The coating material can include an inorganic material. The inorganic material can include at least one selected from the group consisting of soda-lime glass, borosilicate glass, quartz, alumina, Pyrex®, silica, and metal-oxide compounds. The inorganic material can include at least one metal selected from the group consisting of aluminum, chromium, cobalt, copper, gold, iron, manganese, nickel, palladium, platinum, silver, titanium, zinc and zirconium. The inorganic material can be in the form of a powder.

The coating material can vary in thickness. The coating material can have a thickness of from 10-1000 nm. The coating material can have a thickness of 10, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nm, or can be within a range of any high value and low value selected from these values.

The diameter of the microspheres can vary. The diameter of the microspheres can be from 30-300 µm. The diameter of the microspheres can be 30, 40, 50, 60, 70, 80, 90, 100, 110, 120, 130, 140, 150, 160, 170, 180, 190, 200, 210, 220, 230, 240, 250, 260, 270, 280, 290, or 300 µm, or can be within a range of any high value and low value selected from these values.

The pore diameter of the pores can vary. The porous core can have pores having a pore diameter of from 5 nm to 1000 nm. The pore diameter can be 5, 6, 7, 8, 9, 10, 11, 12, 13, 14, 15, 16, 17, 18, 19, 20, 21, 22, 23, 24, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 nm, or can be within a range of any high value and low value selected from these values.

The transition from the first state to the second state can be accomplished by different means. Suitable methods include polymerization, densification and sintering. The transition from the first state to the second state can be performed by melting and resolidifying a polymer coating.

The porosity of the porous core can vary. The porosity of the porous core can be from 25% to 90%. The porosity of the porous core can be 25, 30, 35, 40, 45, 50, 55, 60, 65, 70, 75, 80, 85, or 90%, or can be within a range of any high value and low value selected from these values.

The gas inside the porous core can be at least one selected from the group consisting of air, $H_2$, $H_2S$, $O_2$, CO, $CO_2$, NO, $NO_2$, $NH_3$, $CH_4$, $CO_2$, and mercaptan.

The insulation medium can include matrix material configured to randomly pack the plurality of microspheres in the matrix material. The randomly packed microspheres form a void fraction in a range of 15-99 volume % based upon the total volume of the microspheres and the matrix material. The void fraction can be 15, 20, 25, 30, 35, 40, 45, 50, 55, 60, 65, 70, 75, 80, 85, 90, 95, or 99 volume %, or can be within a range of any high value and low value selected from these values.

The matrix material can be a polymeric material. The matrix polymeric material can include at least one selected from the group consisting of polyolefins, methyl methacrylate copolymer, ethyl methacrylate copolymer, polyvinyl butyral, poly(methyl methacrylate-co-ethyl acrylate), polystyrene, polyvinyl butyral, polyvinyl alcohol, poly(ethylene carbonate), ethylene vinyl alcohol copolymer, polyurethane and epoxies.

Insulation according to the invention includes an insulation medium comprising a plurality of microspheres, each microsphere comprising a porous core comprising a porous core material and having an exterior surface, a gas within the porous core, and a coating layer coating all of the exterior surface of the porous core. The coating layer comprises a coating material which transitions from a first state to a second state, and wherein in the first state the coating material is permeable to the gas, and in the second state the material is impermeable to the gas. The coating material in the second state is configured to encapsulate and maintain partial vacuum of the gas inside the porous core.

The thermal resistance of the insulation can vary. The insulation can have a thermal resistance in a range of 15-400 mK/W. The insulation can have a thermal resistance of 15, 25, 50, 75, 100, 125, 150, 175, 200, 225, 250, 275, 300, 325, 350, 375, or 400 mK/W, or within a range of any high value and low value selected from these values.

A container for the insulation medium can provided to form an insulating structure. The insulating structure can vary. The container for the insulation medium can in one aspect include wall board so as to form a wall panel. The container in another aspect can include paper, for example corrugated paper, so as to be useful for insulated packaging. The insulation medium can include a matrix material configured to randomly pack the plurality of microspheres in the matrix material. The insulation medium can then be incorporated into numerous different structures to provide insulating benefits.

A building panel according to the invention includes a first facing material, a second facing material spaced from the first facing material, and an insulation medium between the first facing panel and the second facing panel. The insulation medium comprises a plurality of microspheres, each microsphere comprising a porous core comprising a porous core material and having an exterior surface, a gas within the porous core, and a coating layer coating all of the exterior surface of the porous core. The coating layer comprises a coating material which transitions from a first state to a second state, and wherein in the first state the coating material is permeable to the gas, and in the second state the material is impermeable to the gas. The coating material in the second state is configured to encapsulate and maintain partial vacuum of the gas inside the porous core.

A method of making an insulation medium can include the step of providing a plurality of microspheres. Each microsphere comprises a porous core comprising a porous core material and having an exterior surface. A gas is positioned within the porous core. A coating layer is applied and coats all of the exterior surface of the porous core to provide a coated porous core. The coating layer comprises a coating material which transitions from a first state to a second state, and wherein in the first state the coating material is permeable to the gas, and in the second state the material is impermeable to the gas. A vacuum is applied to the coated porous core, wherein some of the gas will diffuse through the coating material in the first state to establish a partial vacuum of the gas within the porous core.

The coating material is transitioned from the first state to the second state while maintaining the partial vacuum of the gas within the porous core. The coating in the second state will seal the porous core with the partial vacuum of the gas inside.

The step of applying a coating layer to the porous core can include sputtering the coating material. The step of applying a coating layer to the porous core can include dip-coating the porous core in the coating material. The step of applying a coating layer to the porous core can include fluidized-bed coating of the coating material onto the porous core. Other methods of applying the coating are possible.

The step of transitioning the coating material from the first state to the second state can include at least one selected from the group consisting of polymerization, densification and sintering. The step of transitioning the coating material from the first state to the second state can include heating of the coating material. The method can include the step of embedding the microspheres into a matrix material. Other methods of transition ing the coating from the first state to the second state are possible.

The invention can also be used to store fluids. A fluid storage media according to the invention includes a plurality of microspheres. Each microsphere includes a porous core comprising a porous core material and having an exterior surface. A stored fluid is provided within the porous core. A coating layer coats all of the exterior surface of the porous core. The coating layer comprises a coating material which transitions from a first state to a second state, and wherein in the first state the coating material is permeable to the stored fluid, and in the second state the material is impermeable to the stored fluid. The coating material in the second state is configured to encapsulate and maintain the stored fluid inside the porous core.

The stored fluid pressure in the porous core can be above an ambient pressure surrounding the microspheres. The coating can be biodegradable. The coating material can be selected to degrade at an operating temperature. The coating can be frangible. The fluid storage media can be used with a solvent, and the coating can dissolve in the solvent. Other coatings and methods of releasing the sored contents are possible.

The stored fluid can vary. The stored fluid can include at least one selected from the group consisting of $H_2$, $H_2S$, $O_2$, CO, $CO_2$, NO, $NO_2$, $NH_3$, $CH_4$, $CO_2$, $SO_2$ and mercaptan. The stored fluid can include a gaseous hydrocarbon selected from the group consisting of acetylene, propane, ethylene, and light alkanes. The stored fluid can be a biologically active medication. The stored fluid can include at least one refrigerant selected from the group consisting of fluorocarbons, butane, propane, and ammonia. Other stored fluids are possible.

A method of delivering a fluid can include the step of providing a plurality of microspheres, each microsphere comprising a porous core comprising a porous core material and having an exterior surface. A coating layer is applied and coats all of the exterior surface of the porous core to provide a coated porous core, wherein the coating layer comprises a coating material which transitions from a first state to a second state, and wherein in the first state the coating material is permeable to the fluid, and in the second state the material is impermeable to the fluid. A pressure of the fluid is applied to the coated porous core, wherein some of the fluid will diffuse through the coating material in the first state to establish a quantity of the fluid within the porous core. The coating material is transitioned from the first state to the second state while maintaining the quantity of the fluid within the porous core, wherein the coating in the second state will seal the porous core with the quantity of the fluid inside. The microspheres are delivered to a location. The coating is degraded to release the fluid. The fluid pressure can be applied before the coating material has been applied to the porous core. The fluid pressure can be applied after the coating material has been applied to the porous core.

A method of delivering a biologically active fluid medication to a patient providing a plurality of microspheres according to the invention. A biologically active fluid medication is positioned within the porous core. A coating layer coating is applied to all of the exterior surface of the porous core to provide a coated porous core, wherein the coating layer comprises a coating material which transitions from a first state to a second state, and wherein in the first state the coating material is permeable to the biologically active fluid medication, and in the second state the material is impermeable to the biologically active fluid medication. A fluid pressure of the biologically active fluid medication is applied to the coated porous core, wherein some of the biologically active fluid medication will diffuse through the coating material in the first state to establish a quantity of the biologically active fluid medication within the porous core. The coating material is then transitioned from the first state to the second state while maintaining the quantity of the biologically active fluid medication within the porous cor. The coating in the second state will seal the porous core with the quantity of the biologically active fluid medication inside.

The coating material in the second state can include a biodegradable material, and after being delivered to the body of the patient the coating will biodegrade and deliver the biologically active fluid medication to the patient. The coating material in the second state can be temperature sensitive and degrade at body temperature, such that after being delivered to the body of the patient the coating will degrade at body temperature and deliver the biologically active fluid medication to the patient.

The biologically active material can be a pharmaceutical where the microsphere serves a nanocarrier. These nanocarriers allow for targeted treatment. This includes applications like incorporation of chemotherapeutic agents for cancer therapy, radiographic contrast agents for targeted imaging, and antimicrobials agents to fight infections.

FIG. 1 is a schematic diagram of a microsphere 20 in a first stage of assembly. The microsphere 20 is comprised of a porous core shell 24 which can have a hollow interior 28. The porous includes a number of pores 32 which percolate through the porous core 24 to the hollow interior 28. Air or other fluids 36 are initially trapped within the hollow interior 28. A coating layer 40 in a first state is provided on an exterior surface of the porous core 24. The coating layer 40 coats all of the exterior surface of the porous core. The coating layer 40 comprises a coating material which transitions from a first state to a second state. In the first state the coating material is permeable to the fluid 36, and in the second state the material is impermeable to the fluid 36.

Figure 2:
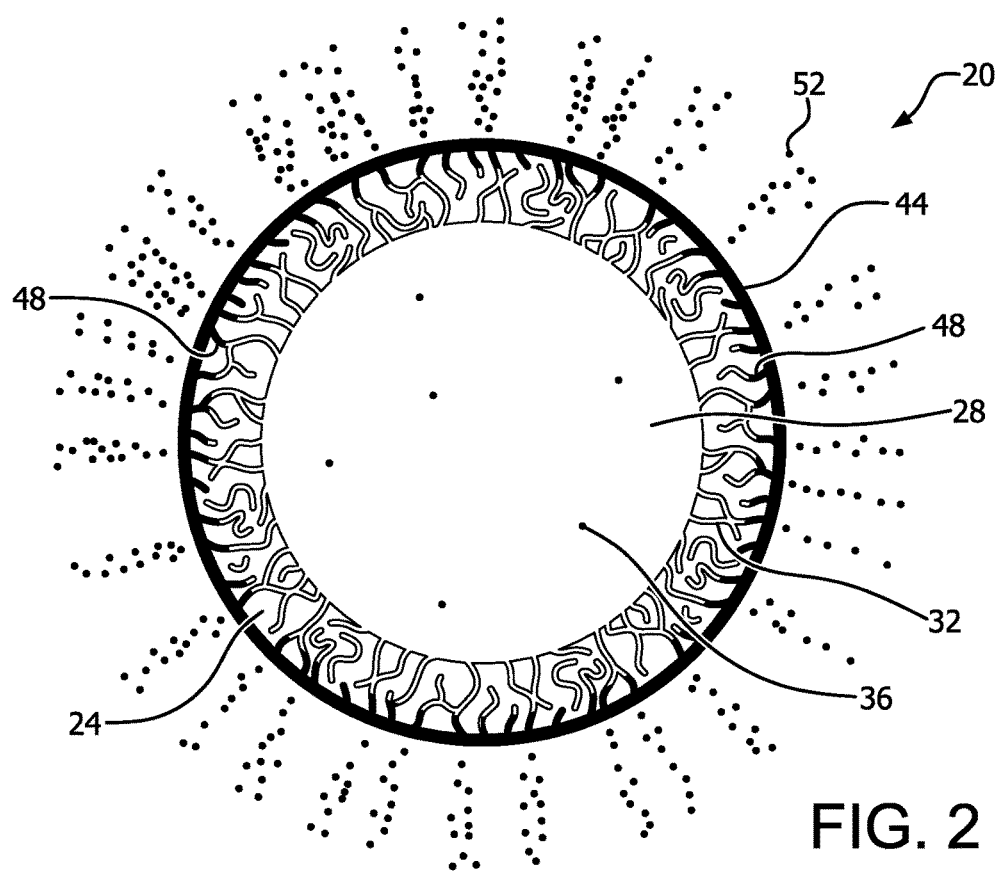
FIG. 2 is a schematic diagram of a microsphere in a second stage of assembly.

There is shown in FIG. 2 a second stage of assembly. The microsphere 20 is placed in a reduced-pressure environment such that the fluid 36 is withdrawn from the hollow interior 28 as particles 52 into the surrounding atmosphere. The coating layer 40 is then transitioned into a second state coating layer 44 which is impermeable to the gas or air. Portions of the coating layer second state 44 enter and plug the pores 32 as shown by plugs 48.

Figure 3:
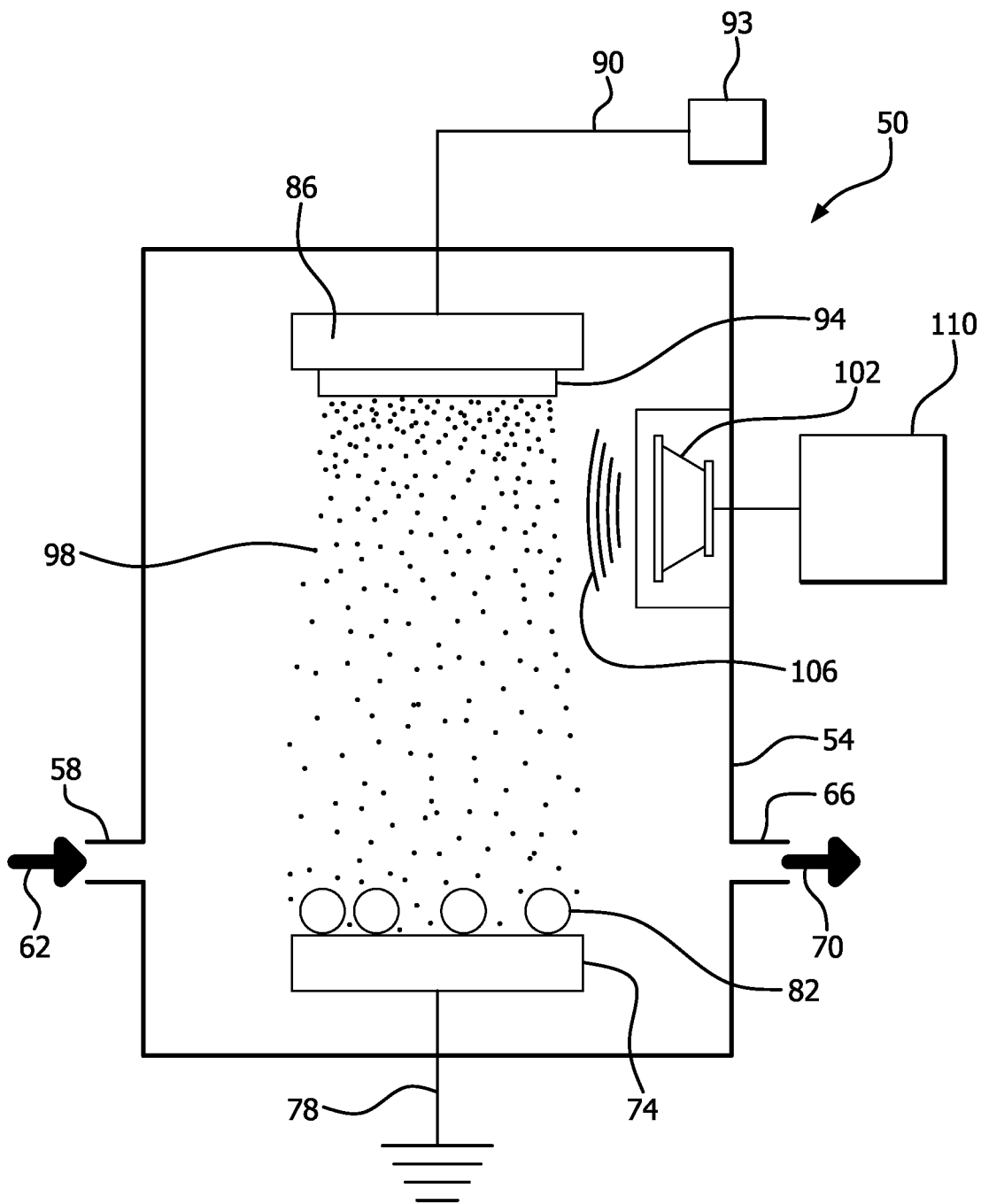
FIG. 3 is a schematic diagram of a first stage of a method of making a microsphere.

The manner of applying the coating layer to the porous core of the microspheres can vary. An apparatus 50 for applying the coating layer to the porous core of the microspheres is shown in FIG. 3. FIG. 3 is a schematic diagram of the device 50 having a housing 54 with an inlet 58 for inlet gas 62 such as Ar used during deposition. An outlet 66 is provided for exhaust gas 70. A support 74 is provided within the housing 54 and connected to ground 78. A second support 86 is provided for a coating layer source 94 and is connected to a voltage source 93 through a connection 90. Upon application of a potential, particles 98 of the coating layer source material 94 are emitted and travel to the porous cores 82 on the support 74. Sonication of the coating particles 98 and porous core 82 can assist in thorough coverage of the coating layer particles 98 on the porous cores 82 to produce the microspheres. Sonication can be provided by suitable structure such as speaker 102 emitting sonic waves 106 and driven by a source electrical supply 110.

Figure 4:
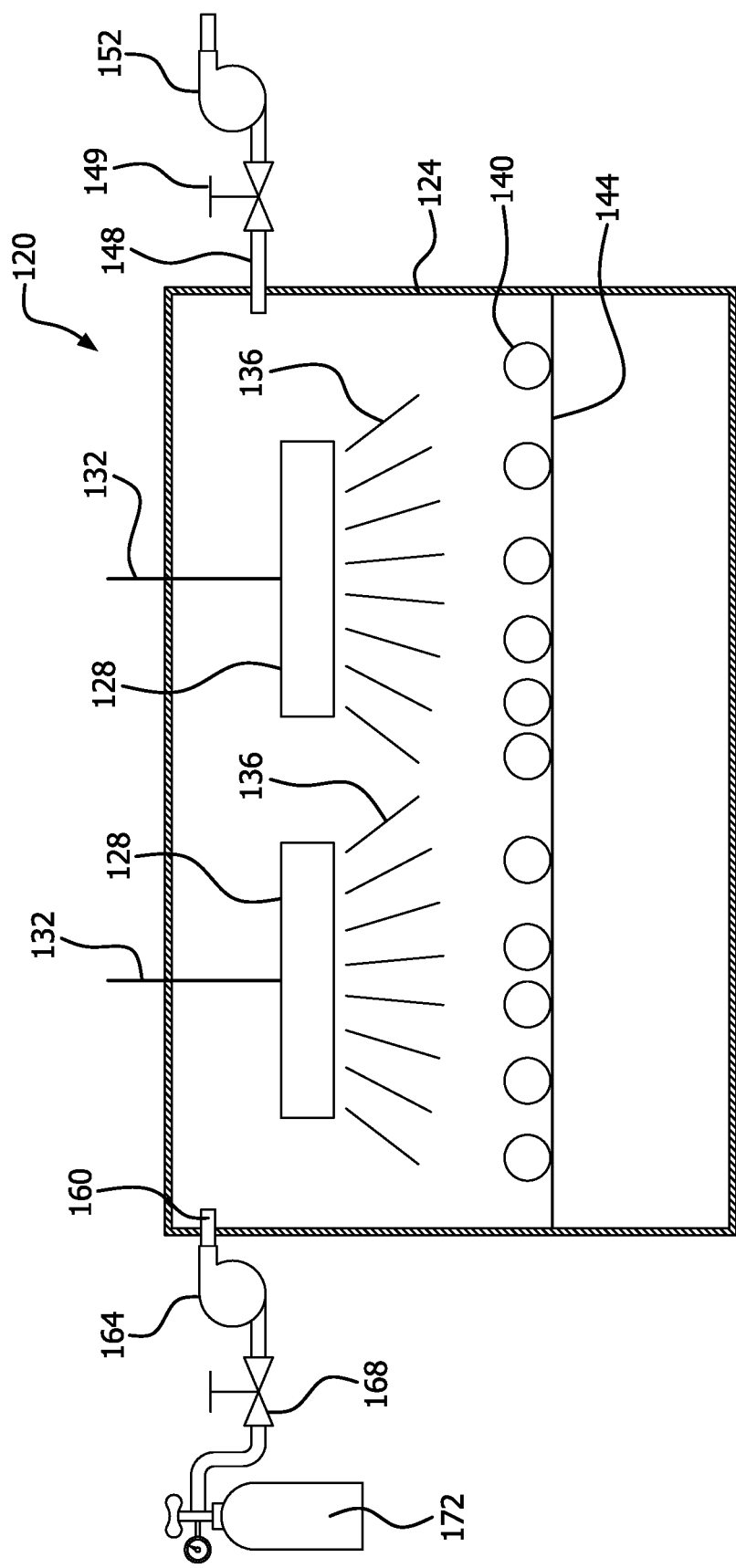
FIG. 4 is a schematic diagram of a second stage of a method of making a microsphere.

The coated microspheres must be treated to evacuate fluid within the porous core and transition the coating layer from the first state to the second state where the coating layer becomes impervious to the fluid. There is shown in FIG. 4 a schematic diagram of an apparatus 120 for transitioning the coated microspheres from the first state to the second state. The apparatus 120 has a housing 124 and can have radiating or heating devices 128 connected to energy sources by connection 132. The radiating devices 128 generate radiant energy 136 which can be light such as ultraviolet light, or heat depending on the nature of the coating material and what is necessary to change the coating material from the first state to the second state. The microspheres 140 are positioned on a support 144 where they are subjected to the radiant energy 136. The support 144 can be moving conveyor for a continuous process, and can also be a vibrating bed to assure even contact the radiant energy around each microsphere 140. A reduced pressure is maintained within the apparatus 120 through a gas outlet 148 which can be connected to a vacuum pump 152 and controlled by valve 149. The apparatus 120 can also be used to store fluid within the microspheres 140, and in such case the gas to be stored in the microspheres can be supplied through an inlet 160 connected to a pressure pump 164, control valve 168 and source 172 of the stored gas.

Figure 5:
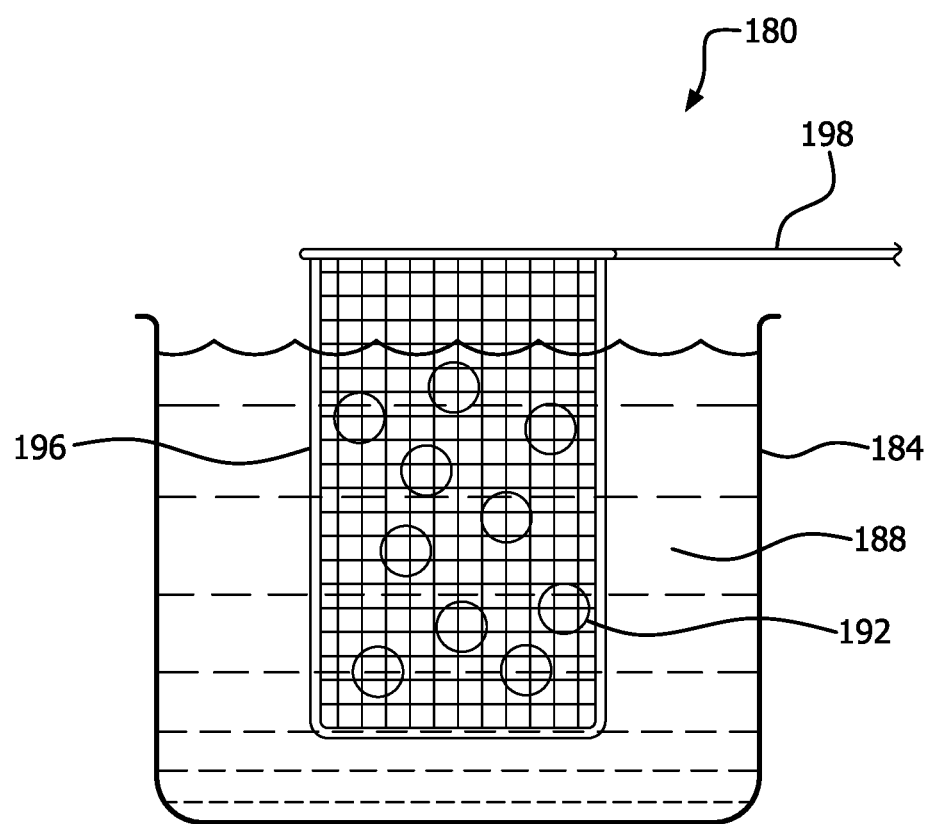
FIG. 5 is a schematic diagram of an alternative method of making a microsphere.

FIG. 5 is a schematic diagram of an alternative method of coating the porous core of the microsphere. The coating device 180 consists of a vat 184 containing the coating material 188. The porous cores 192 are placed within a porous container 196 connected to a support 198. The porous container 196 can be dipped into the vat 184 to coat the porous cores 192 with the coating material 188. The coated microspheres can be removed from the vat 184 and placed into another apparatus such as the apparatus 120 of FIG. 4 to transition the coating from the first state to the second state.

Figure 6:
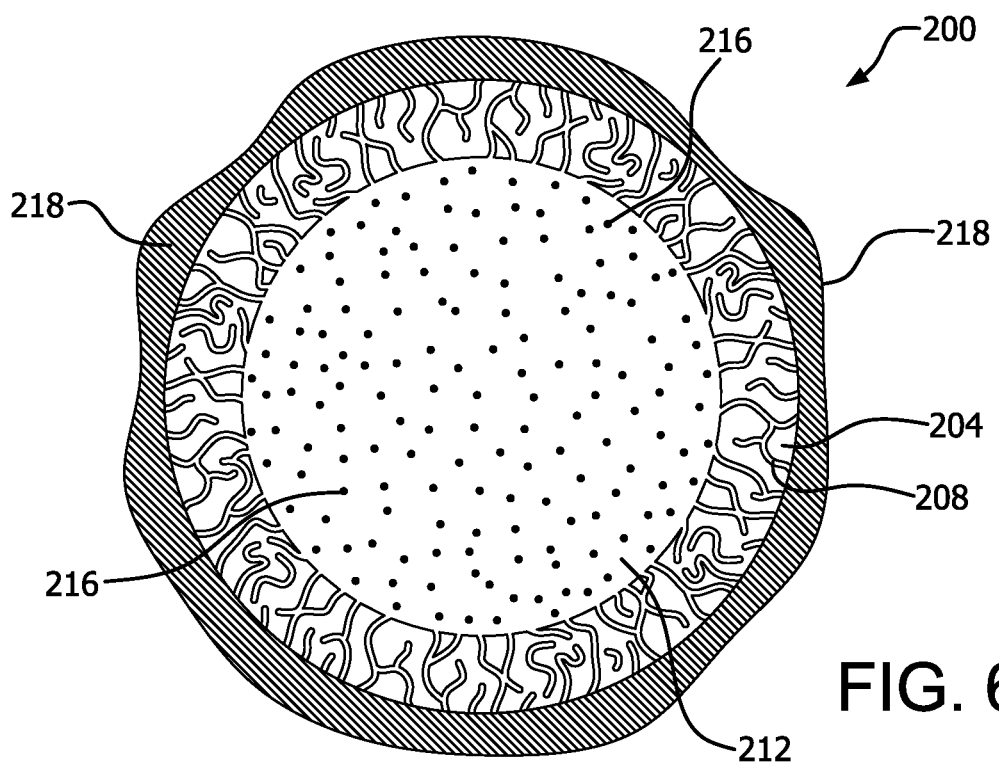
FIG. 6 is a schematic cross-section of an alternative microsphere in a first stage of construction.

Alternative embodiments of the microspheres are possible. There is shown in FIG. 6 a schematic cross-section of an alternative microsphere 200 in a first stage of construction. The microsphere 200 includes a porous core 204 having percolating pores 208 and having an open interior 212. The open interior 212 contains a fluid 216 such as air which must be evacuated to provide a thermally insulating microsphere. A coating layer 218 in a first state is provided over the porous core 204.

Figure 7:
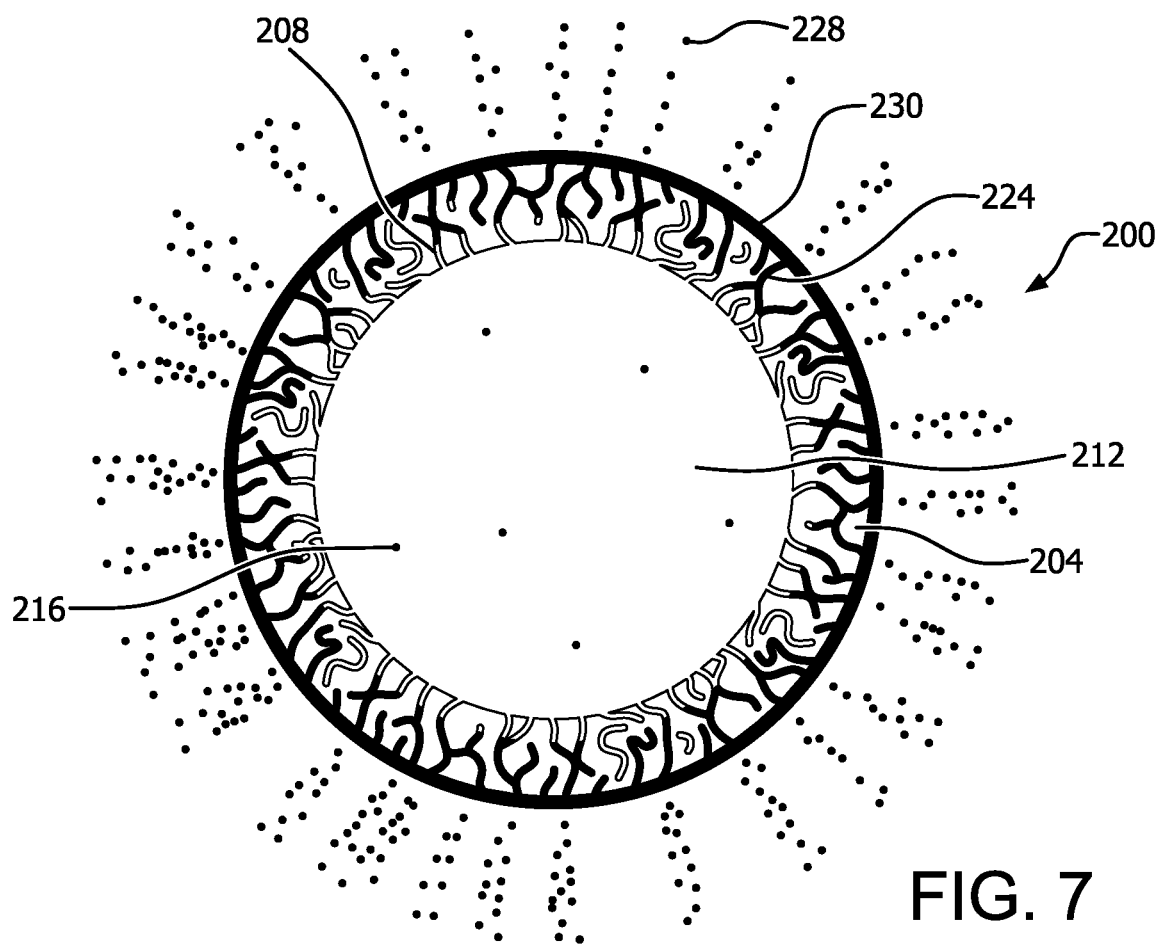
FIG. 7 is a schematic cross-section of an alternative microsphere in the second stage of construction.

FIG. 7 is a schematic cross-section of the microsphere 200 in the second stage of construction. The atmosphere around the microsphere 200 has been evacuated to a reduced pressure. The fluid particles 216 are drawn from the open interior 212, passing through the pores 208 to provide exterior particles 228 which are removed by vacuum pump. The coating layer 218 is a glass material and transitions to a second state coating 230 which is impervious to the fluid particles 216 and the exterior counterparts 228. Some of the coating material enters the pores 208 and becomes plugs 234 which help to seal the microspheres 200.

Figure 8:
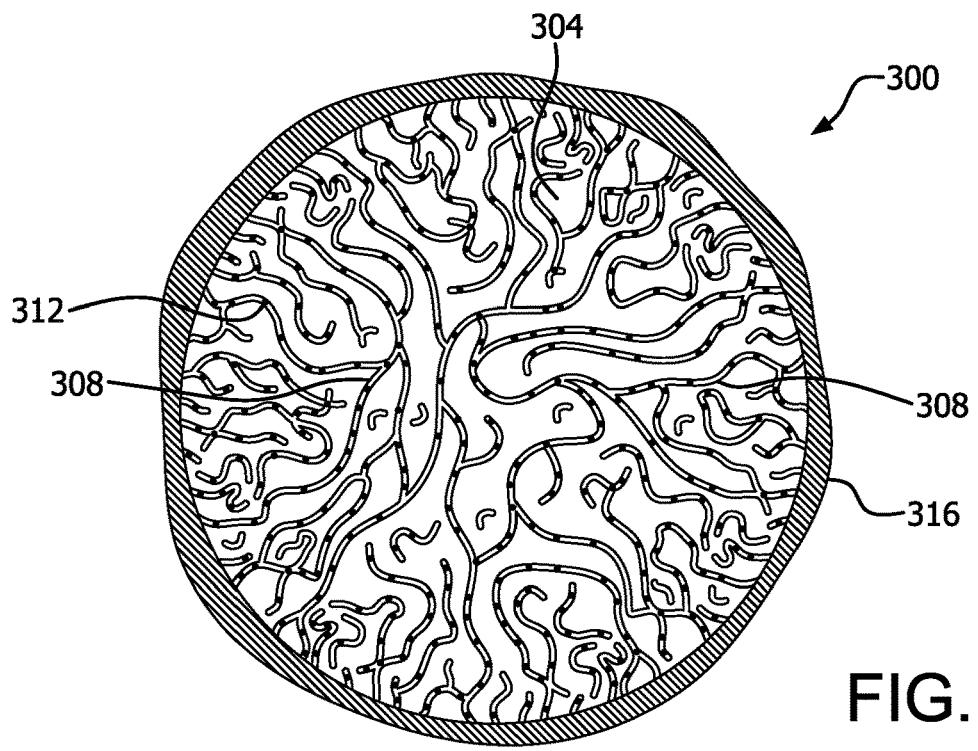
FIG. 8 is a schematic cross-section of a microsphere with a porous core, in a first mode of construction.
Figure 9:
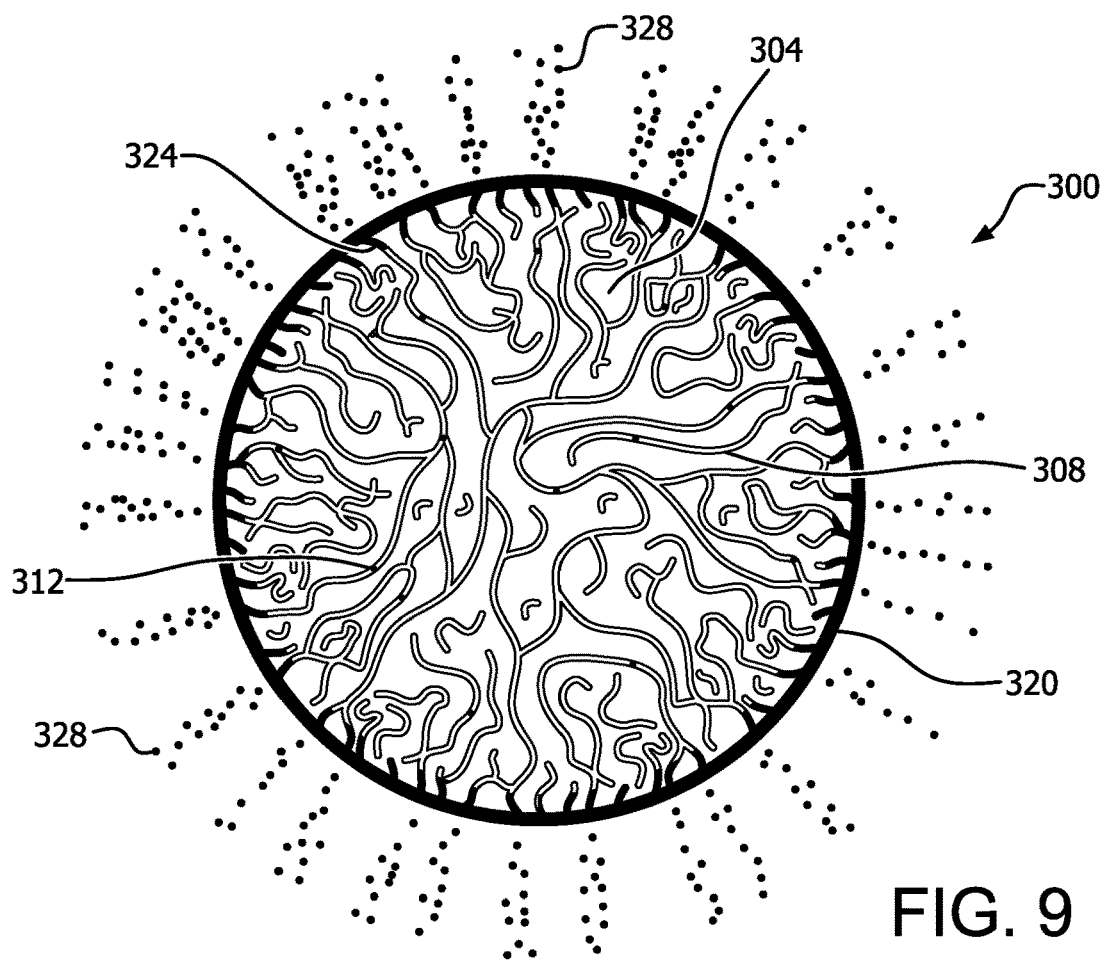
FIG. 9 is a schematic cross-section of a microsphere with a porous core, in a second mode of construction.

There is shown in FIG. 8 is a schematic cross-section of a microsphere 300 with a porous core 304 for lacking a hollow interior, and instead having percolating pores 308 throughout a continuous porous core 304 shaped as a spherical body. Fluid particles 312 are initially within the pores 308. A coating layer 316 coats the exterior surface of the porous core 304. There is shown in FIG. 9 is a schematic cross-section of the microsphere 300 in a second state which the ambient surrounding the microsphere 300 has been evacuated to a reduced pressure drawing the fluid particles 312 from the pores 308 through the coating material 316 to provide exterior particles 328 which are then presented from the surrounding atmosphere. The coating layer 316 is transition to the second state 320 and plugs 324 of the coating material in the second state can partially penetrate the pores 308 to further seal the microsphere 300.

Figure 10:
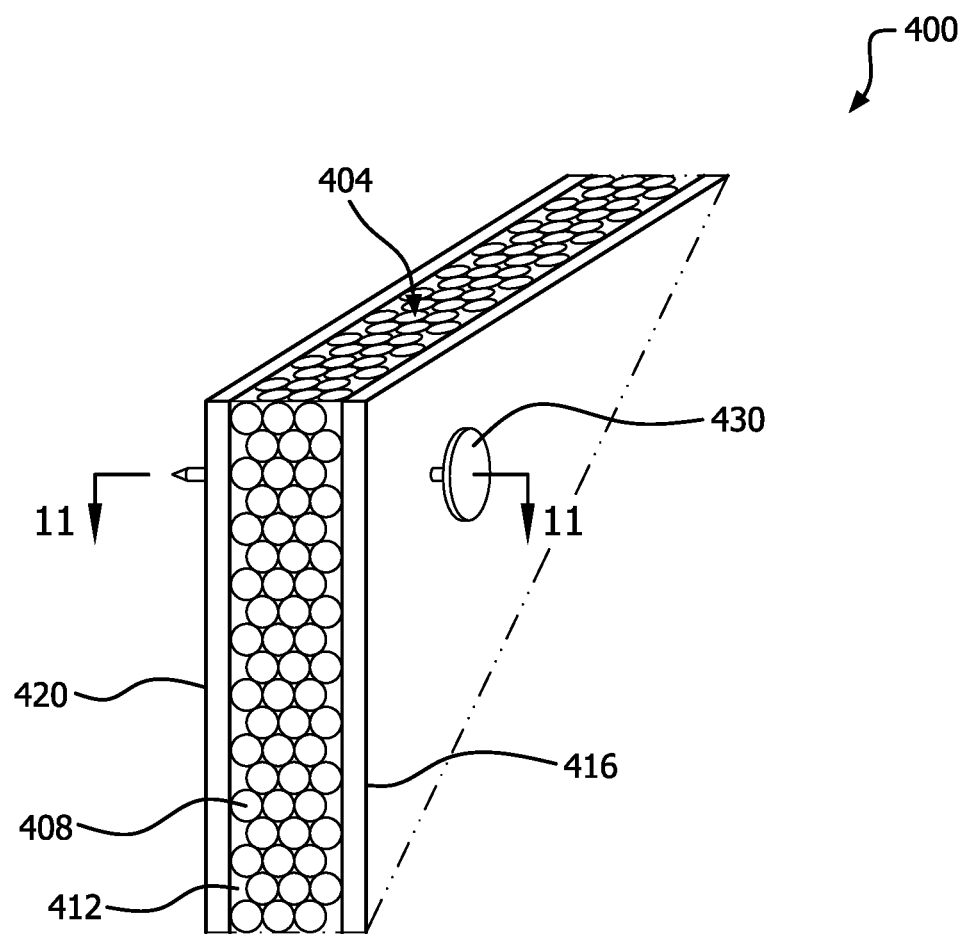
FIG. 10 is cross-section of a wall panel insulated with an insulation medium comprising microspheres according to the invention.
Figure 11:
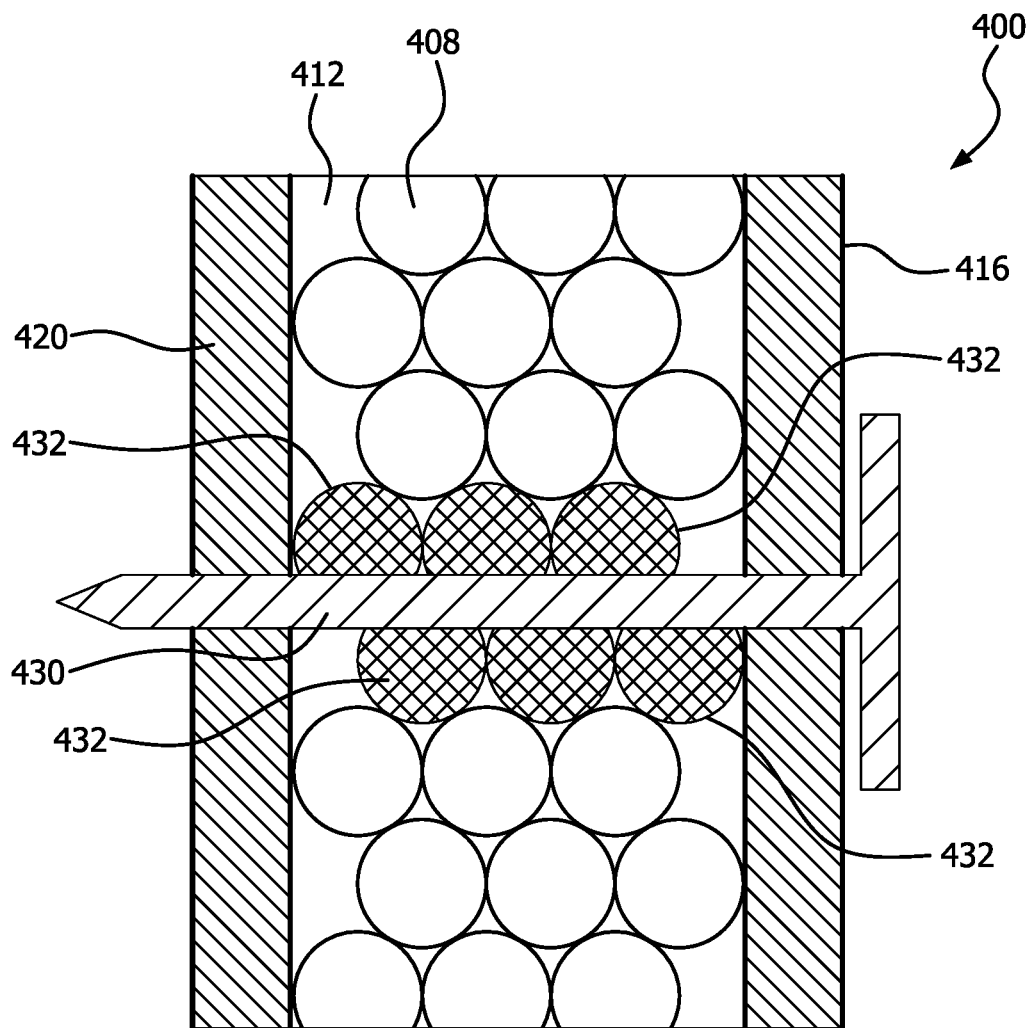
FIG. 11 is a cross-section taken along line 11-11 in FIG. 10.

FIG. 10 is cross-section of a wall panel 400 according to the invention with an insulation medium 404 comprising microspheres 408 embedded in a matrix 412. Insulation 404 can be embedded between wall surfacing panels 416 and 420 which can be made of a material suitable for building construction, such as gypsum, polymeric materials, natural materials such as wood veneers or engineered woods, or other wall surfacing materials. The wall panel 400 can receive nails 430 or other securing and attachment apparatus. As shown in FIG. 11, the nail 430 will rupture microspheres 432 which are positioned in the insulation 404 in the path of the nail 430. Surrounding microspheres, however, remain unaffected and will continue to contribute the insulation of the wall panel 400.

Figure 12:
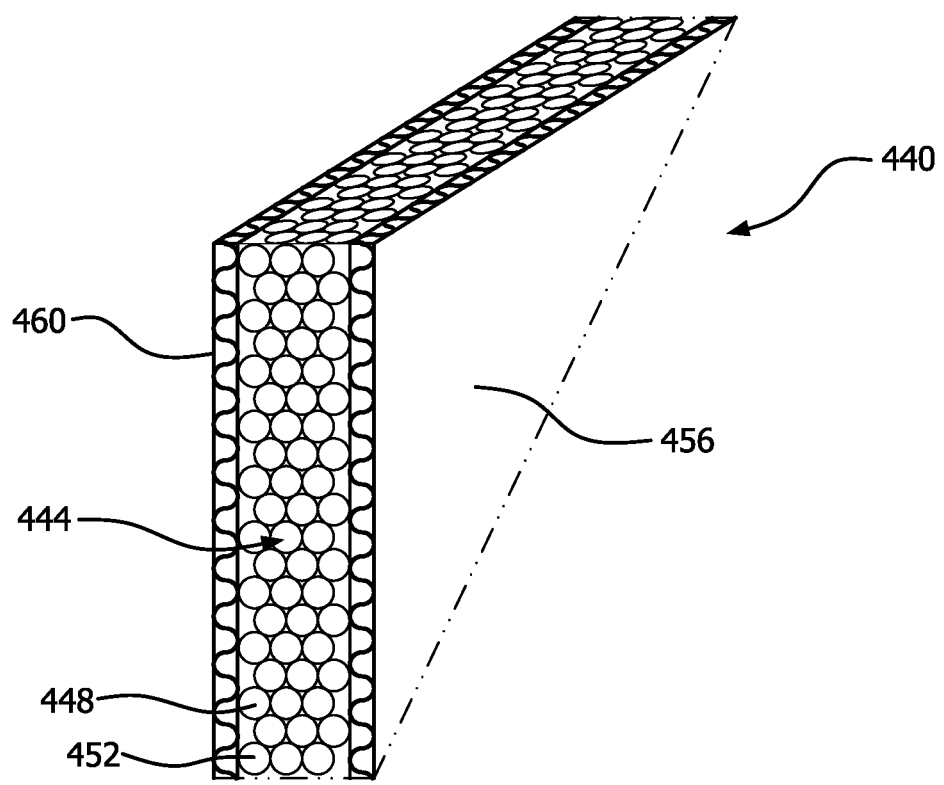
FIG. 12 is a cross-section of an insulated packaging medium according to the invention.

FIG. 12 is a cross-section of an insulated packaging medium 440 which is comprised of an insulation medium 444 according to the invention. Insulation medium 444 which includes microspheres 448 embedded within a matrix 452. Surfaces of the insulation medium 444 can be provided by packaging materials such as corrugated paper 456 and 462. The insulated packaging medium 440 can be shaped, sized, and cut into various forms, and will provide a packaging material that can maintain the heat or cold items stored within the packaging.

Figure 13:
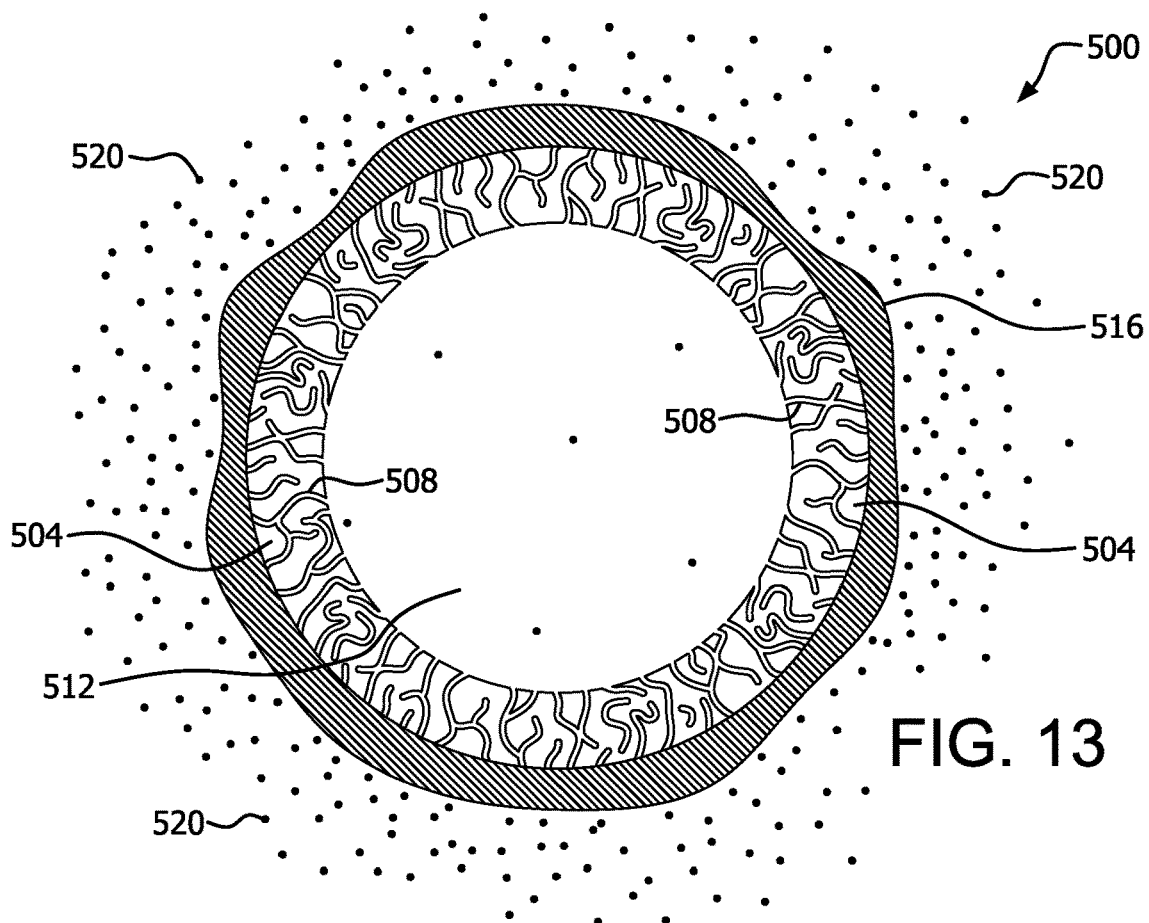
FIG. 13 is a cross-section of a microsphere for storing fluids, in a first stage of construction.
Figure 14:
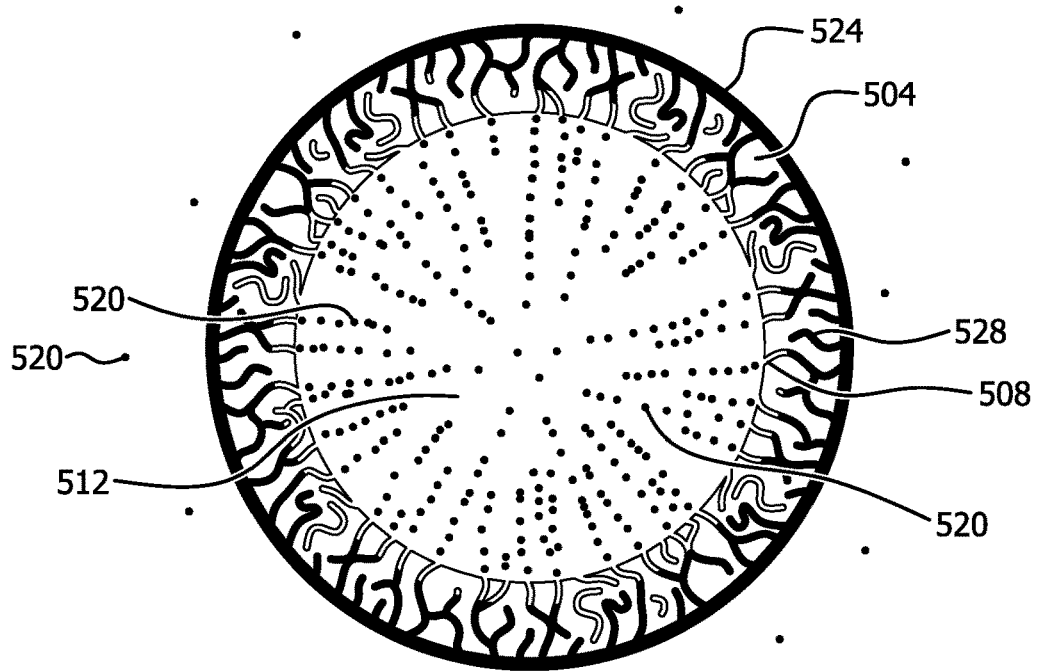
FIG. 14 is a cross-section of a microsphere for storing fluids, in a second stage of construction.

FIG. 13 is a cross-section of a microsphere 500 for storing fluids, in a first stage of construction. The microsphere 500 can have a porous core 504 with percolating pores 508. The porous core 504 can be a porous solid sphere or can have an open interior 512. A coating layer 516 in the first state coats the porous core 504. Fluid particles 520 to be stored are provided in a pressurized environment and pass through the coating layer 516 and the pores 508 into the open interior 512, as shown in FIG. 14. The coating layer 516 is then transitioned from a first state to a second state 524 in which the coating layer is impervious to the stored fluid 520. Portions of the coating layer 524 can penetrate the pores 508 as plugs 528 to further seal the microspheres 500.

Figure 15:
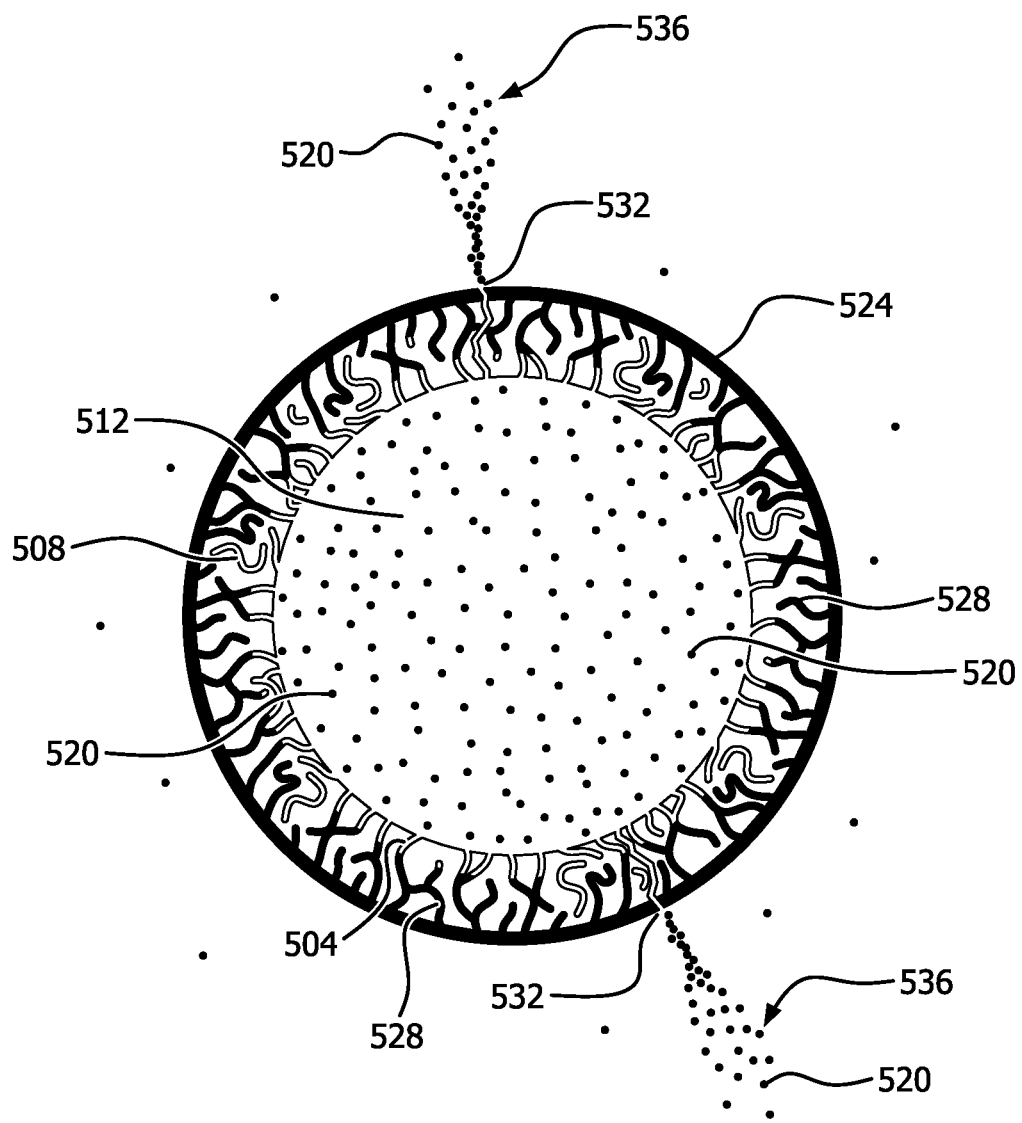
FIG. 15 is a cross-section of a microsphere for storing fluids, in a fluid release mode of operation.

When release of the stored fluid 520 is desired, the coating layer 524 is again transitioned to a state which will permit the release of the stored fluid 520. As shown in FIG. 15, this change of state can be mechanical such as cracks 532 which release the stored fluid 520 as a stream 536.

Figure 16:
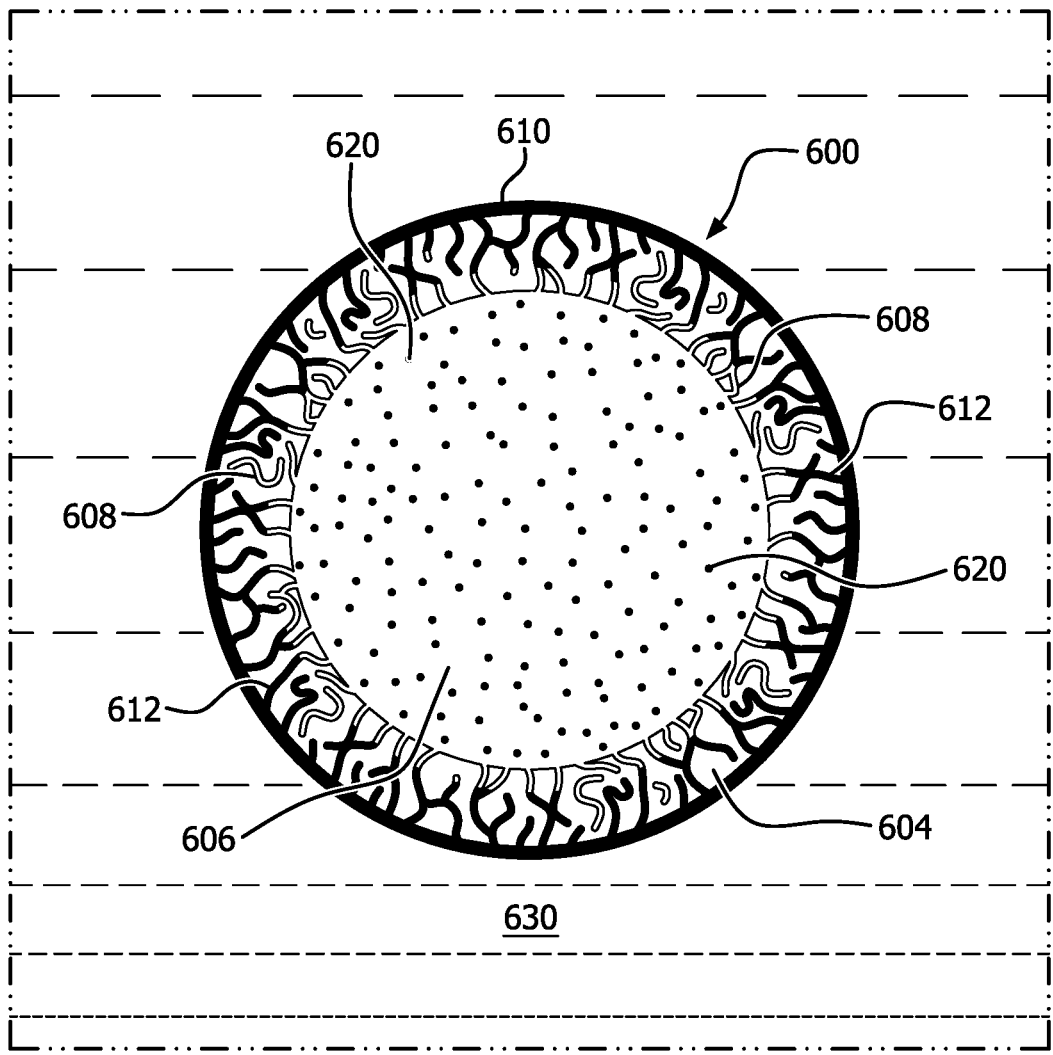
FIG. 16 is a cross-section of a microsphere for storing fluids, in a liquid medium and in a first mode of operation.
Figure 17:
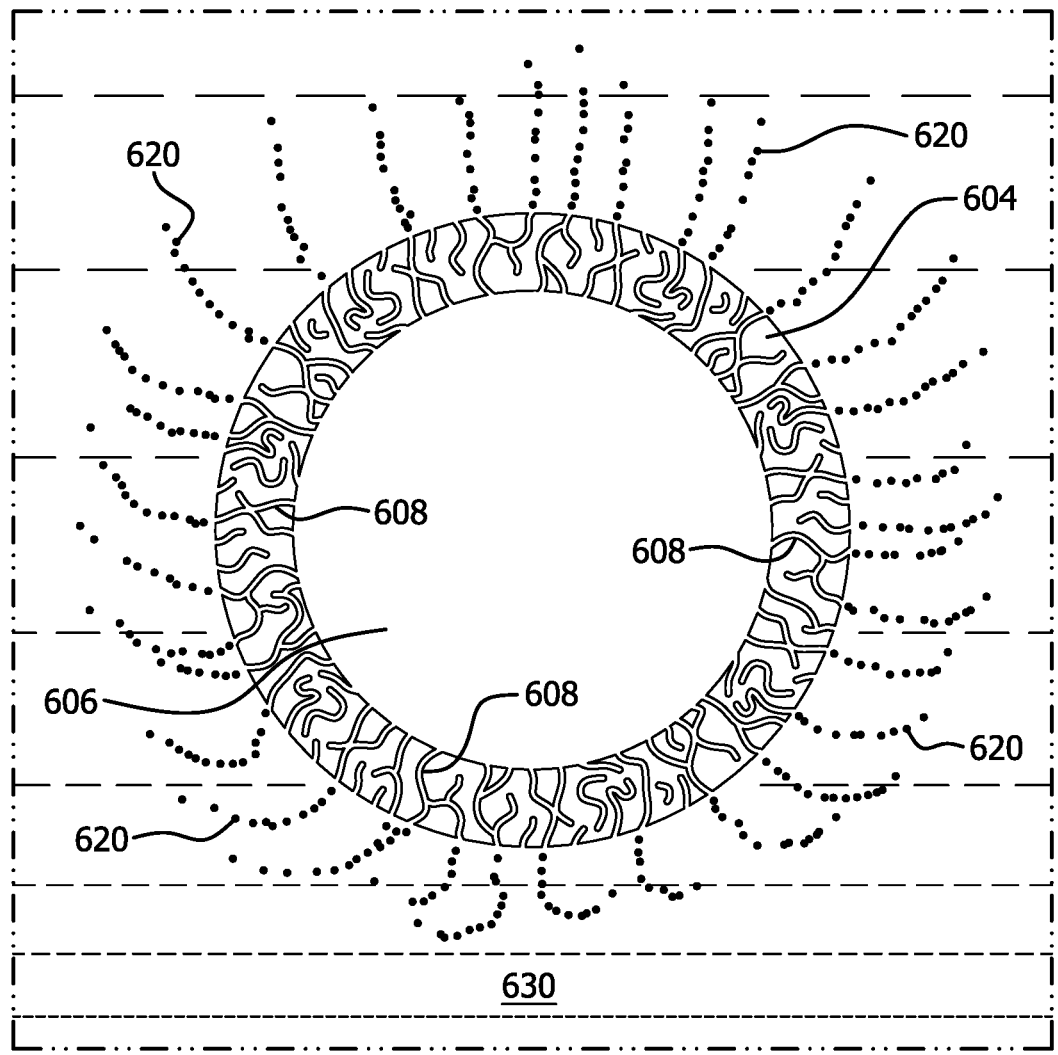
FIG. 17 is a cross-section of a microsphere or storing fluids, in a liquid medium and in a second mode of operation.

The release of the stored fluid can take other forms. As shown in FIG. 16, a microsphere 600 has a porous core 604 with pores 608 and an open interior 606 storing fluid particles 620. A coating layer 610 is in the first state impervious to the stored fluid 620 and can have plugs 612 blocking escape of the stored fluid 620 through the pores 608. The microspheres 600 are placed in an intended fluid medium 630 such as, for example biological fluids such as blood or within the stomach. The material of the coating layer 610 is selected to degrade after contact with such biological fluids. As shown in FIG. 17, a portion of the coating layer 610 degrades and opens at least some of the pores 608 and the stored fluid 620 escapes from the interior 606 into the surrounding biological fluid 630.

Radio-frequency magnetron sputtering was used to deposit thin film glass coatings onto hollow glass microspheres (GL 1756, Mo-Sci Specialty Products) at room temperature using commercial glass targets made by bonding 2 in. diameter pieces of soda-lime or Pyrex to a copper plate. The microspheres (bulk density ~0.35 g/cm$^3$) ranged in diameter from 40 to 90 μm. The internal cavities were bounded by an ~1 μm thick interconnected nanoporous shell structure consisting of 10-300 nm scale pores extending from the insides to the outsides of the shells through the thickness. The targets, mounted onto a Torus Magnetron Source (Kurt J. Lesker) located above the microsphere bed, were sputtered at an applied power of 75-100 W in argon (Ar) (99.9995%) delivered at a flow rate of 20 standard cubic centimeters per minute through a Sierra Instruments mass flow controller. During deposition, the chamber pressure was kept at 20 mTorr and the deposition time was varied from 24 to 96 hours to achieve different coating thicknesses. Approximately 0.5 g of microspheres was placed in a 70 mm aluminum weighing dish that was placed and confined on a repurposed Altec-Lansing sound system. The samples were pumped down to a base pressure $<2\times10^{-6}$ Torr before deposition. The speaker was wired through the deposition chamber and connected to a laptop where music was played at various intensities. The randomness and the intensity of the sonic vibrations caused the microspheres to fluidize and tumble below the deposition source, exposing all the external surfaces to the deposition flux. The deposited species rained onto the surfaces of the microspheres, where they nucleated and grew into a glass film coating. Growth was confined to the outer surfaces of the microspheres, as the fluidized nature, surface diffusion, and limited line-of-sight distances for the deposited atoms prevented the deposited species from penetrating deeply into the pores of the microsphere shells. Following deposition, the coated microspheres were annealed either in a vacuum furnace (under 10 mTorr) or in 1 Atm of Ar at temperatures ranging from 700° C. to 740° C. for 4 h to produce a complete, dense coating coverage on the exterior surfaces of the microspheres, yielding either a vacuum or Ar trapped inside the hollow cores.

The surfaces and cross-sectional morphologies of coated and uncoated microspheres were evaluated by a Zeiss Merlin VP high-resolution field-emission scanning electron microscope (SEM) equipped with an energy-dispersive x-ray spectroscopy (EDX) unit. The phase identity of the coatings was characterized by a PANalytical Empyrean series-2 x-ray diffractometer (XRD) with copper Kα radiation operating at 45 kV and 40 mA in the range of 5–70°. For surface area and pore size analysis, nitrogen ($N_2$) adsorption isotherms were measured at liquid nitrogen temperature (77 K) using a 3Flex Surface Characterization Analyzer (Micromeritics). The samples were dried and degassed under vacuum at a temperature of 120-150° C. and a vacuum pressure of 5 mbar using a Smartvac Prep Station (Micromeritics) for a minimum of 16 h before the dry mass was recorded and the isotherms collected. The surface area was calculated using the Brunauer-Emmett-Teller (BET) method in the relative pressure range of 0.007-0.02, and the pore size distributions were obtained using the Barrett-Joyner-Halenda (BJH) method. A hot disk transient plane source (TPS) method was used to measure the thermal conductivities of the reference polyurethane (PU) and CEIS-loaded PU specimens. The volume fraction of CEIS in the composite was about 40% and the specimens were 12 mm in diameter and 10-12 mm thick. A hot-disk sensor (double-spiral, 10 μm thick, nickel alloy wire covered with 25 μm thick Kapton insulation) was sandwiched between a Styrofoam block (a material with known thermal conductivity) and the specimen. Measurements (in single-side mode) were conducted using a commercial TPS3500 instrument with a 3.189 mm radius sensor that served as both a heat source and a temperature sensor. To improve the sensor-specimen contact, an estimated load of 1-2 Newton was applied over the test assembly. During the measurements, a constant electric power (25 mW) was applied for a duration of 20 s; and the thermal transport properties of the specimens were calculated by recording the change in temperature over time. Alternatively, to demonstrate the gas trapping ability, Ar-filled microspheres were dispersed on a plastic tray and loaded inside a vacuum chamber, which was pumped overnight to a background pressure on the order of $10^{-8}$ Torr and monitored by an ionization gauge. After the ion gauge reading was stabilized overnight, the particles were crushed with the aid of a pneumatic actuator while the change in chamber pressure was monitored.

Hollow glass microspheres with an interconnected porous shell structure were chosen as they provided an ideal material system that enabled gas diffusion into and out of the hollow interior either to create an internal vacuum or to store specific gases, once they were sealed with appropriate coating agents. The basic approach to fabrication began with the deposition of uniform glass coatings onto sonically vibrated microspheres using magnetron sputtering. Following film deposition, microspheres were heat-treated under vacuum (or in a gas ambient) to achieve a dense conformal coating coverage on the outer surfaces of the microspheres. Since grain growth is a kinetically driven diffusion-controlled process, annealing at temperatures above the softening point of the coated material enabled smaller grains to evolve into well-connected larger grains owing to grain growth and coalescence, forming a continuous and highly dense glass coating over the microspheres. To assess the influence of the deposited thickness and subsequent post-deposition heat treatment on the microstructural evolution of the coatings, representative SEM images of the 30 nm and 300 nm thick soda-lime and Pyrex coatings on the microspheres were taken. Note that, because of its higher thermal and mechanical properties, samples coated with Pyrex (softening point ~820° C.) were heat-treated at a relatively higher temperature than their counterparts coated with soda-lime (softening point ~725° C.); the temperatures were 740° C. for Pyrex and 700° C. for soda-lime.

While the as-deposited thinner coatings for each glass type exhibited fine-grained but porous coverage over the microspheres, samples with thicker coatings displayed a continuous, well-connected larger-grained structure assembled by coalescence of the smaller grains. The corresponding cross-sectional SEM images of the latter samples illustrated a dense columnar grain growth morphology for both soda-lime and Pyrex coatings and highlight the interpenetrating nature of the porous shell structure of the microspheres. Upon thermal treatment in vacuum, irrespective of the coating material, there was a stark contrast between the thinner and thicker film surface morphologies. Although both glass films appeared to be much smoother as a result of the softening and the pronounced kinetically driven diffusion at elevated temperatures, the granular film microstructure for the thicker coatings evolved into a nearly featureless, compact, dense surface morphology (associated with the grain growth). Samples with thinner deposits exhibited high porosity (i.e., holes) within the film matrix.

To determine the vacuum level of coated microsphere, a test to understand whether the coating applied to the microspheres successfully seals the pores and maintains a consistent environment in the hollow interior of the particles was conducted. The strategy first involved filling the microspheres with an inert gas (Ar), followed by high temperature annealing in flowing Ar to densify the coating through kinetic diffusion. After the thermal treatment process, particles were loaded in a vacuum chamber that was capable of producing very low vacuum values on the order of $10^{-8}$ Torr. This chamber enabled crushing of the particles by a pneumatically controlled mechanism while monitoring the vacuum level. Hence, if the particles were not sealed effectively, their hollow interior would be evacuated in the chamber and no change in vacuum level should be observed. On the other hand, if the microspheres were sealed well, then the Ar gas would be released during the crush test, resulting in an increase in the chamber pressure.

To confirm this strategy, microspheres coated with soda-lime glass were annealed at 700° C. for 4 hr in Ar at 1 atm, during which the microspheres were filled with Ar. The microspheres were transferred to the vacuum chamber and pumped for 2 h, and then crushed upon releasing the pneumatic actuator. An increase in chamber pressure (monitored by a vacuum gauge) from $1.43\times10^{-8}$ to $1.73\times10^{-8}$ Torr was observed, suggesting that Ar was released from the crushed particles. This result indicates that the soda-lime coating is dense and effectively seals the particles, which in turn prevents gas leakage from the microsphere. To confirm that the microspheres were crushed during the test, the microstructures of the particles were compared before and after crushing. It was observed that microspheres were completely broken into pieces after the crush test.

The invention as shown in the drawings and described in detail herein disclose arrangements of elements of particular construction and configuration for illustrating preferred embodiments of structure and method of operation of the present invention. It is to be understood however, that elements of different construction and configuration and other arrangements thereof, other than those illustrated and described may be employed in accordance with the spirit of the invention, and such changes, alternations and modifications as would occur to those skilled in the art are considered to be within the scope of this invention as broadly defined in the appended claims. In addition, it is to be understood that the phraseology and terminology employed herein are for the purpose of description and should not be regarded as limiting.

We claim:

1. A method of making a fluid storage media, comprising the steps of:
    providing a plurality of microspheres, each microsphere comprising a porous core comprising a porous core material and having an exterior surface;
    applying a coating layer covering all of the exterior surface of the porous core to provide a coated porous core, wherein the coating layer comprises a coating material which transitions from a first state to a second state, and wherein in the first state the coating material is permeable to the fluid, and in the second state the material is impermeable to the fluid;
    applying a fluid to the coated porous core, wherein some of the fluid will diffuse through the coating material in the first state to establish a portion of the fluid within the porous core;
    transitioning the coating material from the first state to the second state while maintaining the fluid within the porous core, wherein the coating in the second state will seal the porous core with the fluid inside.

2. The method of claim 1, wherein the step of applying a coating layer to the porous core comprises sputtering the coating material.

3. The method of claim 1, wherein the step of applying a coating layer to the porous core comprises dip-coating the porous core in the coating material.

4. The method of claim 1, wherein the step of applying a coating layer to the porous core comprises fluidized-bed coating of the coating material onto the porous core.

5. The method of claim 1, wherein the step of transitioning the coating material from the first state to the second state comprises at least one selected from the group consisting of polymerization, densification and sintering.

6. The method of claim 1, wherein the step of transitioning the coating material from the first state to the second state comprises heating of the coating material.

7. The method of claim 1, wherein the stored fluid within the porous core has a fluid pressure, and the fluid pressure in the porous core is above an ambient pressure surrounding the microspheres.

8. The method of claim 1, wherein the coating is biodegradable.

9. The method of claim 1, wherein the coating material degrades at an operating temperature.

10. The method of claim 1, wherein the coating is frangible.

11. The method of claim 1, further comprising a solvent, and wherein the coating dissolves in the solvent such that the porous core is no longer sealed, wherein the fluid will be released from the porous core.

12. The method of claim 1, wherein the stored fluid comprises at least one selected from the group consisting of H2, H2S, O2, CO, CO2, NO, NO2, NH3, CH4, CO2, SO2 and mercaptan.

13. The method of claim 1, wherein the stored fluid comprises a gaseous hydrocarbon selected from the group consisting of acetylene, propane, ethylene, and light alkanes.

14. The method of claim 1, wherein the stored fluid is a biologically active medication.

15. The method of claim 1, wherein the stored fluid comprises at least one refrigerant selected from the group consisting of fluorocarbons, butane, propane, and ammonia.

16. The method of claim 1, wherein in the second state the coating is impermeable to air.

17. The method of claim 1, wherein the porous core comprises a structure of interconnected pores or channels, and the coating material conformally coats the exterior of the porous core to form a gas-impermeable layer that maintains pressure inside the porous core.

18. The method of claim 1, wherein the porous core comprises at least one selected from the group consisting of glass, diatomaceous earth, calcium silicate and polymers.

19. The method of claim 1, wherein the glass comprises at least one selected from the group consisting of borosilicate, quartz, borosilicate glass and soda lime.

20. The fluid storage media of claim 1, wherein the porous core is shaped as a hollow shell comprising a porous shell wall.

21. The method of claim 20, wherein a thickness of the shell wall is from 0.5-5 μm.

22. The method of claim 1, wherein the coating material comprises a polymeric material.

23. The method of claim 22, wherein the polymeric material comprises at least one selected from the group consisting of methyl methacrylate copolymer, ethyl methacrylate copolymer, polyvinyl butyral, poly(methyl methacrylate-co-ethyl acrylate), polystyrene, polyvinyl butyral, polyvinyl alcohol, poly(ethylene carbonate), ethylene vinyl alcohol copolymer, polyurethane and epoxies.

24. The method of claim 1, wherein the coating material comprises an inorganic material.

25. The method of claim 24, wherein the inorganic material comprises at least one selected from the group consisting of soda-lime glass, borosilicate glass, quartz, alumina, Pyrex®, silica, and metal-oxide compounds.

26. The method of claim 24, wherein the inorganic material comprises at least one metal selected from the group consisting of aluminum, chromium, cobalt, copper, gold, iron, manganese, nickel, palladium, platinum, silver, titanium, zinc and zirconium.

27. The method fluid storage media of claim 24, wherein the inorganic material comprises a powder.

28. The method of claim 1, wherein the coating material has a thickness of from 10-1000 nm.

29. The method of claim 1, wherein a diameter of the microsphere is from 30-300 μm.

30. The method of claim 1, wherein the porous core comprises pores having a pore diameter of from 5 nm to 1000 nm.

31. The method of claim 1, wherein the transition from the first state to the second state comprises melting and resolidifying a polymer coating.

32. The method of claim 1, wherein the porosity of the porous core is from 25% to 90%.

33. The method of claim 1, further comprising embedding the microspheres into a matrix material.

34. The method of claim 33, wherein the matrix material is configured to randomly pack the plurality of microspheres to form a void fraction in a range of 15-99 volume % based upon the total volume of the microspheres and the matrix material.

35. The method of claim 33, wherein the matrix material is polymeric material.

36. The method of claim 35, wherein the matrix polymeric material comprises at least one selected from the group consisting of methyl methacrylate copolymer, ethyl methacrylate copolymer, polyvinyl butyral, poly(methyl methacrylate-co-ethyl acrylate), polystyrene, polyvinyl butyral, polyvinyl alcohol, poly(ethylene carbonate), ethylene vinyl alcohol copolymer, polyurethane and epoxies.

37. The method of claim 1, wherein a pressure of the fluid applied to the coated porous core is greater than a fluid pressure within the porous core.

* * * * *

UNITED STATES PATENT AND TRADEMARK OFFICE
CERTIFICATE OF CORRECTION

| | | |
|---|---|---|
| PATENT NO. | : 12,090,461 B2 | Page 1 of 1 |
| APPLICATION NO. | : 17/509869 | |
| DATED | : September 17, 2024 | |
| INVENTOR(S) | : Tolga Aytug et al. | |

It is certified that error appears in the above-identified patent and that said Letters Patent is hereby corrected as shown below:

On the Title Page

Item (63), should read:
Related U.S. Application Data
(63) Continuation of application No. 17/384,317, filed on Jul. 23, 2021, now Pat. No. 12,005,414.

Signed and Sealed this
Fifth Day of November, 2024

Katherine Kelly Vidal
*Director of the United States Patent and Trademark Office*